United States Patent [19]

Basset et al.

[11] Patent Number: 5,234,873
[45] Date of Patent: Aug. 10, 1993

[54] CATALYST WITH A MORDENITE BASE CONTAINING AT LEAST ONE METAL OF GROUPS IIA, IVB, IIB OR IVA AND ITS USE IN ISOMERIZATION OF A C8 AROMATIC CUT

[75] Inventors: Jean M. Basset; Agnès Choplin, both of Villeurbanne; Francis Raatz, Saint-Avold; Albert Theolier, Decines; Christine Travers, Rueil Malmaison, all of France

[73] Assignee: Institut Francais Du Petrole, Rueil Malmaison, France

[21] Appl. No.: 781,167

[22] PCT Filed: Feb. 26, 1990

[86] PCT No.: PCT/FR90/00132
§ 371 Date: Oct. 16, 1991
§ 102(e) Date: Oct. 16, 1991

[87] PCT Pub. No.: WO90/09845
PCT Pub. Date: Sep. 7, 1990

[30] Foreign Application Priority Data

Mar. 3, 1989 [FR] France .................. 89 02946

[51] Int. Cl.$^5$ ................ B01J 29/18; B01J 29/20
[52] U.S. Cl. .................... 502/66; 502/60; 502/74; 502/78
[58] Field of Search .......... 502/66, 74, 78, 60

[56] References Cited

U.S. PATENT DOCUMENTS

| | | | |
|---|---|---|---|
| 3,598,724 | 8/1971 | Mulaskey | 502/78 |
| 4,501,656 | 2/1985 | Dufresne et al. | 208/111 |
| 4,789,655 | 12/1988 | Travers et al. | 502/66 |
| 4,902,847 | 2/1990 | Juguin et al. | 585/533 |
| 4,935,578 | 6/1990 | Dufresne et al. | 585/739 |
| 4,977,121 | 12/1990 | Dufresne et al. | 502/66 |
| 5,077,254 | 12/1991 | Travers et al. | 502/66 |

FOREIGN PATENT DOCUMENTS 46615 3/1982 European Pat. Off. ........ 502/78

Primary Examiner—Carl F. Dees
Attorney, Agent, or Firm—Millen, White, Zelano & Branigan

[57] ABSTRACT

The invention relates to a catalyst for isomerization of a C8 aromatic cut containing a mordenite characterized in that said mordenite contains at least one metal of groups IIa, IVb, IIb or IVa and is such that:
   its overall Si/Al atomic ratio is between 6 and 15,
   its sodium content by weight relative to the weight of dry mordenite is less than 2000 ppm,
   its elementary mesh volume is between 2.725 and 2.785 nm$^3$,
   its n-hexane adsorption capacity is greater than 0.065 cm$^3$ of liquid/gram,
   its isooctane adsorption capacity is less than 0.068 cm$^3$ of liquid/gram.

The invention also relates to the preparation of this mordenite by grafting on an H-shaped mordenite of at least one organometallic compound of said metal.

19 Claims, No Drawings

CATALYST WITH A MORDENITE BASE CONTAINING AT LEAST ONE METAL OF GROUPS IIA, IVB, IIB OR IVA AND ITS USE IN ISOMERIZATION OF A C8 AROMATIC CUT

This invention relates to a catalyst of aluminosilicate type comprising an H-shaped mordenite whose geometric selectivity has been modified by deposition on the outside surface of its crystals of at least one metal selected from the metals of groups IIa (Be, Mg, Ca, Sr, Ba, Ra), IVb (Ti, Zr, Hf), IIb (Zn, Cd, Hg) and IVa (Ge, Sn, Pb) of the periodic table (Handbook of Chemistry and Physics, 61st edition, 1980–81), optionally at least one metal from group VIII of said table and a matrix and its use in the isomerization reactions of C8 aromatic hydrocarbons. It also relates to the process of preparation of said mordenite.

The catalysts now used industrially in these reactions are essentially based on zeolite ZSM5, by itself or in a mixture with other zeolites, such as mordenite, for example. These catalysts are described in particular in patents U.S. Pat. Nos. 4,467,129, 4,482,773 and EP-B-0138617.

The advantage of zeolite ZSM5 resides in its excellent selectivity of shape, which leads to a great selectivity of paraxylene, the selectivity relative to undesirable secondary dismutation reactions remaining at a very low level. The mordenite is a very active zeolite for the isomerization reaction of the C8 aromatic compounds, in particular more active than the ZSM5, however, it does not have special geometric selectivity properties. This is reflected, whatever its Si/Al ratio may be, by paraxylene selectivities lower than those obtained for zeolite MFI and particularly by very large productions of trimethylbenzene. The production of trimethylbenzene by dismutation is actually favored in the mordenite whose microporous system is more open than that of ZSM5: the openings are at 12 oxygens instead of 10 for ZSM5.

The applicant has discovered that it is possible, thanks to the deposition on the outside surface of the mordenite crystals of at least one metal selected from the metals of groups IIa, IVb, IIb and IVa and in particular of magnesium, titanium, zinc and/or tin, to obtain active and selective catalysts for the isomerization reaction of C8 aromatic compounds. This new preparation procedure imparts to the mordenite very improved geometric selectivity properties, which is reflected by a dramatic inhibition of undesirable secondary reactions such as the dismutation. This new modified mordenite further leads to selectivities, relative to the parasitic reactions of dealkylation, which are less to those of the catalysts based on ZSM5. Thus, the result is solids which exhibit performances in isomerization of C8 aromatic compounds that are not only better than those of the mordenites of the prior art but also at least equivalent, and even superior, to the performances of the catalysts with a ZSM5 base.

The mordenite used in the catalyst of this invention is produced from a mordenite either of the type with small pores or the type with large pores.

The mordenite of the small pore type has a content by weight of sodium relative to the weight of dry mordenite generally between 4 and 6.5%, an overall Si/Al atomic ratio generally between 4.5 and 6.5, an elementary mesh volume generally between 2.76 and 2.80 nm$^3$ (with 1 nm=10$^{-9}$m) and usually adsorbs only molecules of kinetic diameter less than about 4.4×10$^{-10}$m.

The mordenite of the large pore type is distinguished from that of the small pore type by the fact that it can adsorb molecules of kinetic diameter greater than about 6.6×10$^{-10}$m, therefore in particular the benzene molecules, in that its overall Si/Al atomic ratio is generally between 4.5 and 20 and in that its elementary mesh volume is usually between 2.74 and 2.79 nm$^3$.

Before making the porous network of the mordenite selective by deposition of at least one metal from groups IIa, IVb, IIb, IVa, it is preferable to prepare first of all the H-shape of said mordenite with a content by weight of sodium relative to the weight of dry mordenite generally less than 2000 ppm, preferably 1000 ppm and, in a still more preferred manner, 500 ppm, an overall Si/Al atomic ratio between 6 and 15, an elementary mesh volume between 2.725 and 2.785 nm$^3$, an adsorption capacity of n-hexane measured at 0° C. under a pressure of 13 torrs (1.7×10$^3$ Pa) greater than 0.065 cm$^3$ of liquid/gram (cm$^3$ of liquid n-hexane per gram of mordenite) and an adsorption capacity of isooctane measured at 40° C. under a pressure of 26 torrs (3.4×10$^3$ Pa) greater than 0.068 cm$^3$ of liquid/gram. The content by weight of water of the H-shaped mordenite is usually between 5 and 40% and, preferably, between 10 and 30%.

For this purpose, any technique known to one skilled in the art can be used such as, for example, direct acid attack, the calcination in the presence or not of steam of NH$_4$$^+$ form followed by one or more acid attacks, the "calcination(s)-acid attack(s)" cycles, the treatments by fluorosilicates or by SiCl$_4$, etc. In the specific case of the mordenite with small pores, it is necessary to assure that the treatments used have duly led to an opening of the methods.

The deposition of the metal or metals selected from the metals of groups IIa, IVb, IIb and IVa is performed advantageously by grafting by using as a grafting agent at least one organometallic compound of said metal which is, on the one hand, large enough not to penetrate inside the microporous network of the H-shaped mordenite and, on the other hand, able to react with the surface OH groups. In the case of magnesium, compounds of formula MgR$^1$R$^2$ (organomagnesium compounds) in which groups R$^1$ and R$^2$, identical or different, are organic groups of varied overall dimensions and, in general, of large overall dimensions, can be used in particular as grafting agents; by way of nonlimiting examples, the radicals alkyl, aryl, organosilyl vinyl, polynuclear aryl, cycloalkyl, allyl, proporgyl can be cited. When group R$_1$ is one of the groups cited above, group R$_2$ can also be a group of encumbered alkoxy or aryloxy type, such as, for example, a tert-butoxy, o,delta-diphenylphenoxy, o,delta-diisopropyl phenoxy group, etc. . . .

In the case of other metals from group IIa (Be, Ca, Sr, Ba, Ra) and metals from groups IVb (Ti, Zr, Hf), IIb (Zn, Cd, Hg) and IVa (Ge, Sn, Pb), compounds of formula BeR$_2$, CaR$_2$, SrR$_2$, BaR$_2$, RaR$_2$, TiR$_4$, ZrR$_4$, HfR$_4$, CdR$_2$, HgR$_2$, GeR$_4$, SnR$_4$ or PbR$_4$ in which R, identical or different to one another, are organic groups such as those defined above in the case of MgR$^1$R$^2$, also can be used as grafting agents.

In the case of magnesium, a preferred grafting agent is the noted bisneopentyl magnesium Mg(Np)$_2$. Generally after putting the mordenite under vacuum or under inert gas at a temperature greater than 150° C., preferably between 225° and 525° C., for example at 400° C., for 2.5 to 5.5 hours, for example for 4 hours (drying stage), then a reduction of the temperature under vacuum or under inert gas to a temperature between 100° and 200° C., preferably equal to 150° C. (for the gas phase method defined later), or to a temperature between 5° and 35° C., preferably equal to 20° C. (for the liquid phase method defined later), the grafting agent can be grafted on the mordenite by the gas phase method (sublimation of $Mg(Np)_2$) or by the liquid phase method ($Mg(Np)_2$ in solution in a solvent, for example, ether, under vacuum or under inert gas). By the gas phase method, the grafting temperature (temperature at which the grafting is performed) is advantageously greater than 50° C. and, preferably, between 100° and 200° C.; by the liquid phase method said temperature is advantageously greater than the freezing temperature of the solvent used ($-116°$ C. in t he case of ether, for example) and, preferably, between 5° and 35° C. The treatment (grafting) periods are usually longer than 1 minute and are advantageously between 10 and 60 minutes. After grafting, the excess of $Mg(Np)_2$ present in the system is eliminated generally by a purging under vacuum or under inert gas in the case of the gas phase method; in the case of the liquid phase method, it is preferred to eliminate first of all the liquid phase, under vacuum or under inert gas, then the excess of $Mg(Np)_2$ by a rinsing (or washing) with a solvent (such as that employed above).

After this elimination of the reagent excess, the mordenite usually undergoes a heat treatment intended to decompose organic fragments Np linked to the magnesium atoms attached to its outside surface. This treatment is advantageously performed in the presence of oxygen (preferably mixed with an inert gas such as nitrogen) at a temperature greater than about 250° C., preferably at about 350° and, in a more advantageous manner, between about 350° and 600° C.

The optional deposition of other metals from groups IIa, IVb, IIb or IVa instead of or in addition to the magnesium is performed in a manner analogous to that described above for the magnesium by using a suitable grafting agent, such as an organometallic compound.

At the end of the heat treatment, the content by weight of the mordenite of metal from group IIa, IVb, IIb and/or IVa (for example, of magnesium) is preferably between 0.05 and 0.30% and, advantageously, between 0.10 and 0.25%.

Nevertheless, it is possible optionally to adjust the selectivity level of the mordenite by proceeding, if necessary, to one or more additional cycles of "grafting of metal (metals) from groups IIa, IVa, IIb or IVb-calcination," according to the technique described above, to attain contents by weight of metal (metals) from said groups (for example, of magnesium) greater than 0.30% and, if necessary, 1.0%.

The acid properties of the mordenite are not changed by the deposition of said metal (metals) according to the technique described above.

Thus, the mordenite obtained has a content by weight of sodium relative to the weight of dry mordenite less than 2000 ppm, preferably 1000 ppm and, in a still more preferred manner, 500 ppm, an overall Si/Al atomic ratio between 6 and 15 and, preferably, between 7.5 and 13.5 and an elementary mesh volume between 2.725 and 2.785 $nm^3$.

On the other hand, its adsorption capacity for the encumbered or branched hydrocarbons (isooctane, for example) is greatly reduced while its adsorption capacity for the linear hydrocarbons (n-hexane, for example) is not affected. Thus, its adsorption capacity of n-hexane measured at 0° C. under a pressure of 13 torrs ($1.7 \times 10^3$ Pa) is greater than 0.065 $cm^3$ of liquid/gram and, preferably, greater than 0.072 $cm^3$ of liquid/gram; its adsorption capacity of isooctane measured at 40° C. under a pressure of 26 torrs ($3.4 \times 10^3$ Pa) is less than 0.068 $cm^3$ of liquid/gram and, preferably, less than 0.058 $cm^3$ of liquid/gram. This limited adsorption capacity for branched hydrocarbons, such as isooctane, measured at low temperature, does not mean that the C8 aromatic compounds do not penetrate the porous volume of the mordenite during the isomerization reaction at high temperature. Actually, it indicates that there will be a strict diffusional limitation for the trimethylbenzenes at high temperature.

The characteristics of the mordenite can be measured by the following methods:

the adsorption capacities are established by gravimetric analysis, the Si/Al atomic ratios are determined by infrared spectrometry, the sodium contents by atomic adsorption, the elementary mesh volume is determined by X diffraction, the mordenite sample being prepared as in the operating mode of standard ASTM D 3942 80 established for the faujasite.

The mordenite can be subjected (before or after the deposition of at least one metal selected from the metals of groups IIa, IVb, IIb and IVa) to the deposition of at least one metal from group VIII, preferably selected in the group formed by platinum and palladium, and shaped by any technique known to one skilled in the art. It can in particular be mixed with a matrix, generally amorphous, for example, with a moist powder of alumina gel. The mixture is then shaped, for example, by extrusion through a die. The mordenite content of the support (mordenite+matrix) thus obtained is generally between about 0.5 and 99.99% and advantageously between about 40 and 90% by weight relative to the support. It is more particularly between about 60 and 85% by weight relative to the support. The matrix content of the catalyst is generally between about 0.01 and 99.5%, advantageously between about 10 and 60% and, preferably, between about 15 and 40% by weight relative to the support (mordenite+matrix).

The shaping can be performed with matrices other than the alumina, such as, for example, magnesium, silica-alumina, natural clays (kaolin, bentonite) and by techniques other than extrusion, such as pelletizing or coating.

The hydrogenating metal of group VIII, preferably Pt and/or Pd, is then deposited on the support by any process known to one skilled in the art and making possible the deposition of the metal on the mordenite. It is possible to use the technique of cation exchanger with competition, where the competing agent is preferably ammonium nitrate, the competition ratio being at least equal to about 50 and advantageously about 50 to 200. In the case of platinum or palladium, a tetraamine complex of platinum or a tetraamine complex of palladium is usually used; the latter will then be deposited practically as a whole on the mordenite. This technique of cation exchange can also be used to deposit the metal directly on the mordenite powder, before its optional mixing with a matrix.

The deposition of the metal (or metals) of group VIII is followed in general by a calcination under air or oxygen, usually between 300° and 600° C. for 0.5 to 10 hours, preferably between 350° and 550° C. for 1 to 4 hours. It is possible then to proceed to a reduction under hydrogen, generally at a temperature between 300° and 600° C. for 1 to 10 hours; preferably, the operation will be performed between 350° and 550° C. for 2 to 5 hours. The metal content of group VIII (preferably Pt and/or Pd) deposited on the catalyst and obtained at the end of the exchange is usually between 0.05 and 1.5%, preferably between 0.1 and 1%, by weight relative to the entire catalyst.

It is also possible to deposit the platinum and/or the palladium no longer directly on the mordenite but on the aluminum binder, before or after the shaping stage, by using an anion exchange with hexachloroplatinic acid, hexachloropalladic acid and/or palladium chloride in the presence of a competing agent, for example, hydrochloric acid. In general, after the deposition of platinum and/or palladium, the catalyst is subjected, as above, to a calcination then reduced under hydrogen as indicated above.

The bifunctional catalyst obtained by the preceding procedures can be used in particular in the isomerization reactions of a C8 aromatic cut, comprising, for example, either only a mixture of xylenes or a mixture of xylene or xylenes and ethylbenzene. The isomerization of alkyl aromatic compounds, and in particular xylenes, assumes a considerable commercial importance. In general, particularly the paraxylene is the most desired product, because it is used in particular as an intermediary in the production of polyester fibers. It is preferred to produce paraxylene by isomerizing metaxylene, which can be obtained by isomerization of orthoxylene. Ethylbenzene, which can be separated with difficulty by distillation of the mixture of xylenes (the boiling points of the various compounds are very close), is very often in the isomerization batch of the C8 aromatic hydrocarbons.

The operating conditions of the isomerization process of a C8 aromatic cut performed in the presence of at least one catalyst according to the invention are usually as follows:

temperature between 240° and 600° C., preferably between 350° and 510° C., pressure between 0.5 and 100 bars, preferably between 2 and 30 bars, space velocity (pph), by batch weight per unit of catalyst batch and per hour, between 0.5 and 200, preferably between 2 and 100, molar ratio of hydrogen to hydrocarbons of batch ($H_2/HC$) between 0.5 and 12, preferably between 2 and 6.

The following examples illustrate the invention without, however, limiting the scope; they are given for a batch formed from 75% of orthoxylene and 25% of ethylbenzene (% by weight).

EXAMPLE 1

Catalysts A1 and A2 according to the invention

The basic material used is a "large pore" mordenite, referenced Zeolon 100 Na of the Norton company; it has an overall Si/Al atomic ratio equal to 6.0, a sodium content by weight relative to the weight of dry mordenite of about 4.5%, an elementary mesh volume of 2.780 $nm^3$, it can absorb, moreover, molecules of kinetic diameter greater than about $6.6 \times 10^{-10}$ m.

This mordenite first of all undergoes an ion exchange in a solution of 10N $NH_4NO_3$ at about 100° C. for 4 hours; then, the solid obtained is subjected to three acid attacks with 0.5N hydrochloric acid, at about 20° C., for 4 hours, volume V of the engaged hydrochloric acid solution being equal to 20 times the weight of dry mordenite (V/P=20 $cm^3/g$).

At the end of these treatments, the H-shaped mordenite has an overall Si/Al atomic ratio equal to 9.0, a sodium content by weight relative to the weight of dry mordenite of 350 ppm, an elementary mesh volume of 2.762 $nm^3$, an n-hexane adsorption capacity (at 0° C., under 13 torrs ($1.7 \times 10^3$ Pa)) of 0.075 $cm^3$ of liquid/g and an isooctane adsorption capacity (at 40° C., under 26 torrs ($3.4 \times 10^3$ Pa)) of 0.070 $cm^3$ of liquid/g.

Then, magnesium is deposited on the outside surface of the crystals of the H-shaped mordenite by gas phase method (i) and by liquid phase method (ii).

i) Gas phase method.

The procedure is performed according to the following successive stages:

putting the mordenite under vacuum at 400° C. for 4 hours, dropping under vacuum to 150° C., putting the mordenite in contact for 30 minutes with a tank brought to 150° C. containing $Mg(Np)_2$ (sublimation stage), isolation of the mordenite and elimination of the excess $Mg(Np)_2$ by vacuum pumping at 150° C., increase to 450° C. with a mixture of 95% $N_2$+5% $O_2$, then passage under pure air at 450° C. and holding under air at this temperature for 2 hours, dropping under air to room temperature (about 20° C.).

The solid obtained at the end of these treatments is referenced HM1: its magnesium content by weight is 0.16%, its n-hexane adsorption capacity (at 0° C., under 13 torrs ($1.7 \times 10^3$ Pa)) is 0.075 $cm^3$ of liquid/g and its isooctane adsorption capacity (at 40° C., under 26 torrs ($3.4 \times 10^3$ Pa)) is 0.038 $cm^3$ of liquid/g, its other characteristics remaining unchanged relative to those of the H-shaped mordenite ii) Liquid phase method The procedure is performed according to the following successive stages:

putting the mordenite under vacuum at 400° C. for 4 hours, dropping under vacuum to 20° C., putting the mordenite under argon in contact for 25 minutes at 20° C. with a solution of $Mg(Np)_2$ in the ether, elimination under argon of the liquid phase, washing by a fresh ether solution, increase to 450° C. under a mixture of 95% $N_2$+5% $O_2$, then passage under pure air at 450° C. and holding under air at this temperature for 2 hours, dropping under air to room temperature (about 20° C.).

The solid obtained at the end of these treatments is referenced HM2: its magnesium content by weight is 0.15%, its n-hexane adsorption capacity (at 0° C., under 13 torrs ($1.7 \times 10^3$ Pa)) is 0.074 $cm^3$ of liquid/g and its isooctane adsorption capacity (at 40° C., under 26 torrs ($3.4 \times 10^3$ Pa)) is 0.039 $cm^3$ of liquid/g, its other characteristics being unchanged relative to those of the H-shaped mordenite.

Two solids HM1 and HM2 then undergo the same treatments: they are each mixed intimately with the alumina on which 0.3% by weight of platinum has been dispersed, the support consisting of the mordenite HM1-alumina (or mordenite HM2-alumina) mixture containing 39% by weight of alumina. The platinum content by weight of each of final catalysts A1 (containing HM1) and A2 (containing HM2) is therefore about 0.12%.

The catalysts thus produced are then shaped by pelletizing, calcined under air at 500° C. for 2 hours and reduced under hydrogen at 500° C. for 3 hours.

These catalysts A1 and A2 are then tested by isomerization of the orthoxylene mixture (75% weight) and ethylbenzene (25% weight), at a temperature of 420° C., under a pressure of 15 bars, with a space velocity (pph) of 50 (hour)$^{-1}$ and a hydrogen to hydrocarbons ($H_2$/HC) molar ratio of about 4.

The performances of catalysts A1 and A2 (and prepared catalysts in the following examples), recorded in table I, are defined by:

$$\text{Conversion of o-xylene (\%)} = \frac{\text{Weight of o-xylene in the batch-weight of o-xylene in the recipe}}{\text{Weight of o-xylene in the batch}} \times 100$$

$$\text{Selectivity in isomerization (\%)} = \frac{\text{Weight of m-xylene and weight of p-xylene}}{\text{Weight of products}} \times 100$$

$$\text{Output in isomerization (\%)} = \frac{\text{Conversion} \times \text{selectivity}}{100}$$

$$\text{Selectivity in dismutation (\%)} = \frac{\text{Weight of trimethylbenzene + weight of toluene + weight of benzene}}{\text{Weight of the products}} \times 100$$

$$\text{Selectivity in cracking (\%)} = \frac{\text{Weight of the gases of C1 to C4}}{\text{Weight of the products}} \times 100$$

EXAMPLE 2

Catalyst B according to the invention

The raw material used is a "small pore" mordenite, referenced Alite 150 of the Societe Chimique de la Grande Paroisse. Its chemical formula in the anhydrous state is: Na $AlO_2(SiO_2)_{5.5}$, its sodium content by weight relative to the weight of dry mordenite is about 5.3%, its elementary mesh volume is 2.790 nm$^3$; it adsorbs only molecules of a diameter at most equal to $3.8 \times 10^{-10}$m 50 grams of this powder is dipped in a 2M solution of ammonium nitrate and the suspension is brought to 95° C. for 2 hours.

The volume of the engaged ammonium nitrate solution is equal to 4 times the weight of dry mordenite (V/P=4 cm$^3$/g). This cation exchange operation is begun again 3 times. After the third exchange, the product is washed with water at 20° C. for 20 minutes, with a V/P ratio equal to 4. The sodium content, expressed in percentage by weight relative to the weight of dry solid, goes from 5.5 to 0.1%. The product is then filtered and subjected to a calcination in confined atmosphere ("self-steaming") at 600° C. for 2 hours (the calcination atmosphere containing at least 5% of steam).

Then, an acid attack is initiated: the solid is refluxed in an aqueous solution of 0.58N hydrochloric acid at 90° C. for 2 hours, with a V/P ratio equal to 8 cm$^3$/g (where V is the volume of the hydrochloric acid solution and P is the weight of dry mordenite). The product is then filtered, washed with 0.1N hydrochloric acid then with water.

The thus obtained H-shaped mordenite has an overall Si/Al atomic ratio equal to 12, a sodium content by weight relative to the weight of dry mordenite of 300 ppm, an elementary mesh volume of 2,750 nm$^3$, an n-hexane adsorption capacity (at 0° C., under 13 torrs ($1.7 \times 10^3$ Pa)) of 0.075 cm$^3$ of liquid/g and an isooctane adsorption capacity (at 40° C., under 26 torrs ($3.4 \times 10^3$ Pa)) of 0.071 cm$^3$ of liquid/g.

Magnesium is then deposited on the outer surface of the crystals of said H-shaped mordenite according to the liquid phase method described in example 1. The obtained mordenite then has a magnesium content by weight of 0.17%, an n-hexane adsorption capacity (at 0° C., under 13 torrs ($1.7 \times 10^3$ Pa)) of 0.075 cm$^3$ of liquid/g and an isooctane adsorption capacity (at 40° C., under 26 torrs ($3.4 \times 10^3$ Pa)) of 0.039 cm$^3$ of liquid/g, its other characteristics remaining unchanged relative to those of the H-shaped mordenite.

The stages of mordenite-alumina mixing, dispersion of the platinum, shaping, reduction of the catalyst and the isomerization test conditions are identical with those described in example 1.

The performances of thus obtained catalyst B (whose platinum content by weight is about 0.12%) are recorded in table I.

EXAMPLE 3

Catalyst C not according to the invention

Catalyst C differs from catalysts A1 and A2 in that the H-shaped mordenite, obtained from the "large pore" mordenite referenced zeolon 100 Na, does not undergo a magnesium deposition.

The stages of mordenite-alumina mixing, dispersion of the platinum, shaping, reduction of the catalyst and the isomerization test conditions are identical with those described in example 1.

The performances of thus obtained catalyst C (whose platinum content by weight is about 0.12%) are recorded in table I.

EXAMPLE 4

Catalyst D not according to the invention

Catalyst D contains a zeolite of MFI structure, synthesized in a fluoride medium; this zeolite has an overall Si/Al atomic ratio of 250. Its sodium content by weight is 50 ppm relative to the weight of dry zeolite. Its elementary mesh volume is equal to 5.360 nm$^3$. Its n-hexane adsorption capacity (at 0° C., under 13 torrs ($1.7 \times 10^3$ Pa)) is 0.071 cm$^3$ of liquid/g and its isooctane adsorption capacity (at 40° C., under 26 torrs ($3.4 \times 10^3$ Pa)) is 0.028 cm$^3$ of liquid/g.

The stages of zeolite-alumina mixing, dispersion of the platinum, shaping, calcination, reduction of the catalyst and the isomerization test conditions are identical with those described in example 1, but with a pph of 30 (hours)$^{-1}$.

The performances of thus obtained catalyst D (whose platinum content by weight is about 0.12%) are recorded in table I.

Catalysts A1, A2 and B according to the invention are more high-performing than catalysts C and D of the prior art: the isomerization output of the C8 aromatic compounds of catalysts A1, A2 and B is clearly greater than that of catalysts C and D. Catalyst D is thus much less active than catalysts A1, A2 and B and catalyst C is not very selective; in particular, with the mordenites made selective according to the invention (catalysts A1, A2 and B), the secondary dismutation reaction leading to the formation of trimethylbenzenes is very greatly inhibited relative to what is obtained in the presence of mordenite not made selective (catalyst C).

TABLE I

| Catalyst | A1 | A2 | B | C | D |
|---|---|---|---|---|---|
| Example | 1 | 1 | 2 | 3 | 4 |
| pph (h$^{-1}$) | 50 | 50 | 50 | 50 | 30 |
| Conversion (%) of o-xylene | 70.5 | 71.0 | 71.0 | 79.5 | 50.0 |
| Isomerization selectivity (%) | 80.1 | 80.2 | 80.0 | 27.0 | 91.5 |
| Isomerization output (%) | 56.5 | 56.9 | 56.8 | 21.5 | 45.7 |
| Dismutation selectivity (%) | 7.0 | 6.8 | 6.8 | 55.0 | 5.5 |
| Cracking selectivity (%) | 1.5 | 1.6 | 1.6 | 1.7 | 0.8 |

Approximately the same results were obtained as those obtained with catalysts A1, A2 and B by replacing the magnesium first of all by titanium, then by zinc and finally tin.

We claim:

1. An aluminosilicate catalyst containing a mordenite, wherein said mordenite contains at least one group IIa, IVb, IIb or IVA metal and is such that:
   its Si/Al atomic ratio is between 6 and 15,
   its sodium content by weight relative to the weight of dry mordenite is less than 2000 ppm,
   its elementary mesh volume is between 2.725 and 2.785 nm$^3$,
   its n-hexane adsorption capacity measured at 0° C. under a pressure of 13 torrs (1.7×10$^3$ Pa) is greater than 0.068 cm$^3$ of liquid/gram,
   its isooctane adsorption capacity measured at 40° C. under a pressure of 26 torrs (3.4×10$^3$ Pa) is less than 0.068 cm$^3$ of liquid/gram.

2. A catalyst according to claim 1, wherein said mordenite has an n-hexane adsorption capacity measured at 0° C. under a pressure of 13 torrs (1.7×10$^3$ Pa) greater than 0.072 cm$^3$ of liquid/gram and an isooctane adsorption capacity measured at 40° C. under a pressure of 26 torrs (3.4×10$^3$ Pa) less than 0.058 cm$^3$ of liquid/gram.

3. A catalyst according to claim 1, wherein the content by weight of said mordenite in said metal is between 0.05 and 0.30%.

4. A catalyst according to claim 1, wherein said metal is a group IIa or IIb metal.

5. A catalyst according to claim 1, wherein said metal is magnesium.

6. A catalyst according to claim 1, further containing at least one group VIII metal.

7. A catalyst according to claim 6, wherein said group VIII metal is platinum or palladium.

8. A catalyst according to claim 1, further containing a matrix.

9. A process of preparation of a mordenite contained in a catalyst according to one of claims 1 to 8 starting from an H-form mordenite in which the deposition of group IIa, IVb, IIb or IVa metal is performed by grafting on said H-form mordenite of at least one organometallic compound of said metal.

10. A process of preparation of a mordenite contained in a catalyst according to one of claims 6 to 8 starting from an H-form mordenite in which the deposition of the group IIa, IVb, IIb or IVa metal is performed by grafting at least one organometallic compound of said metal on said H-form mordenite after the prior deposition on said mordenite of at least one metal of group VIII.

11. A process according to claim 9 in which said grafting takes place in gas phase, by sublimation of said organometallic compound, at a temperature greater than 50° C.

12. A process according to claim 9 in which said grafting takes place in liquid phase, said organometallic compound being in solution in a solvent, at a temperature greater than the freezing temperature of said solvent.

13. A process according to claim 11, comprising the following successive stages:
   a) said mordenite is dried under vacuum or under inert gas between 225° and 525° C. for 2.5 to 5.5 hours,
   b) the temperature is reduced under vacuum or under inert gas to a temperature between 100° and 200° C.,
   c) said mordenite is contacted with said organometallic compound at a temperature between 100° and 200° C. for 10 to 60 minutes,
   d) the organometallic compound excess is eliminated by a purging under vacuum or under inert gas,
   e) the solid obtained in stage d) is put through a heat treatment in the presence of oxygen at a temperature greater than about 250° C.

14. A process according to claim 12, comprising the following successive stages:
   a) said mordenite is dried under vacuum or under inert gas between 225° and 525° C. for 2.5 to 5.5 hours,
   b) the temperature is reduced under vacuum or under inert gas to a temperature between 5° and 35° C.,
   c) said mordenite is contacted under vacuum or under inert gas with said organometallic compound in solution in a solvent at a temperature between 5° and 35° C. for 10 to 60 minutes,
   d) the liquid phase under vacuum or under inert gas is eliminated,
   e) the organometallic compound excess is eliminated by a rinsing with a solvent such as the one used in stage c),
   f) the solid obtained in stage e) is put through a heat treatment in the presence of oxygen at a temperature greater than about 250° C.

15. A process according to claim 9, in which said metal is a metal of groups IIa or IIb.

16. A process according to claim 9 in which said metal is magnesium.

17. A process according to claim 16 in which said organometallic compound is bisneopentyl magnesium Mg(Np)$_2$.

18. A catalyst according to claim 5, further containing at least one metal of group VIII of the periodic table.

19. A catalyst according to claim 18, wherein said metal of group VIII is platinum or palladium.

* * * * *